(12) United States Patent
Rozental et al.

(10) Patent No.: US 11,619,543 B2
(45) Date of Patent: Apr. 4, 2023

(54) POLYMER-COATED HIGH-INDEX WAVEGUIDE FOR ACOUSTIC SENSING

(71) Applicant: TECHNION RESEARCH & DEVELOPMENT FOUNDATION LIMITED, Haifa (IL)

(72) Inventors: Amir Rozental, Haifa (IL); Resmi Ravi Kumar, Haifa (IL); Shai Tsesses, Nesher (IL); Assaf Grinberg, Binyamina (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 74 days.

(21) Appl. No.: 17/269,343

(22) PCT Filed: Aug. 20, 2019

(86) PCT No.: PCT/IL2019/050935
§ 371 (c)(1),
(2) Date: Feb. 18, 2021

(87) PCT Pub. No.: WO2020/039436
PCT Pub. Date: Feb. 27, 2020

(65) Prior Publication Data
US 2021/0325237 A1 Oct. 21, 2021

Related U.S. Application Data

(60) Provisional application No. 62/720,050, filed on Aug. 20, 2018.

(51) Int. Cl.
*G01H 9/00* (2006.01)
*A61B 5/00* (2006.01)
(Continued)

(52) U.S. Cl.
CPC .......... *G01H 9/004* (2013.01); *A61B 5/0095* (2013.01); *G02F 1/0134* (2013.01); *G02F 1/11* (2013.01); *A61B 5/0084* (2013.01); *G02F 1/0131* (2013.01)

(58) Field of Classification Search
CPC .... G01H 9/004; A61B 5/0095; A61B 5/0084; G02F 1/0134; G02F 1/11; G02F 1/0131
See application file for complete search history.

(56) References Cited

U.S. PATENT DOCUMENTS

| 2003/0223672 | A1 | 12/2003 | Joyner et al. | |
|---|---|---|---|---|
| 2014/0114187 | A1* | 4/2014 | Rozental | A61B 8/44 600/407 |
| 2014/0301706 | A1* | 10/2014 | Ballato | G02B 6/03694 65/435 |

FOREIGN PATENT DOCUMENTS

JP        2001350036 A        12/2001

OTHER PUBLICATIONS

Hossain, Md Faruque, et al. "Generalized characteristics of photo-elastic birefringence in polymer strip waveguides." Optical Materials Express 5.5 (2015): 1030-1044. (Year: 2015).*

(Continued)

*Primary Examiner* — Dominic J Bologna
(74) *Attorney, Agent, or Firm* — The Roy Gross Law Firm, LLC; Roy Gross

(57) ABSTRACT

Apparatus is provided including an acoustic sensor (50) having an optical waveguide (20). The optical waveguide (20) includes a waveguide core (202) having a waveguide core refractive index and a waveguide core photo-elastic coefficient, and an over-cladding layer (204) coupled to the waveguide core (202) and including an optically transparent polymer having an over-cladding refractive index and an over-cladding photo-elastic coefficient. The waveguide core refractive index is greater than the over-cladding refractive (Continued)

index, and the over-cladding photo-elastic coefficient is greater than the waveguide core photo-elastic coefficient. Other applications are also described.

20 Claims, 8 Drawing Sheets

(51) Int. Cl.
    *G02F 1/01*         (2006.01)
    *G02F 1/11*         (2006.01)

(56) References Cited

OTHER PUBLICATIONS

Campopiano, Stefania, et al. "Underwater acoustic sensors based on fiber Bragg gratings." Sensors 9.6 (2009): 4446-4454. (Year: 2009).*
English machine translation of Imamura JP2001350036A (Year: 2000).*
Campopiano, S., Cutolo, A., Cusano, A., Giordano, M., Parente, G., Lanza, G., & Laudati, A. (2009). Underwater acoustic sensors based on fiber Bragg gratings. Sensors, 9(6), 4446-4454.
Moccia, M., Pisco, M., Cutolo, A., Galdi, V., Bevilacqua, P., & Cusano, A. (2011). Opto-acoustic behavior of coated fiber Bragg gratings. Optics express, 19(20), 18842-18860.
Rosenthal, A., Omar, M., Estrada, H., Kellnberger, S., Razansky, D., & Ntziachristos, V. (2014). Embedded ultrasound sensor in a silicon-on-insulator photonic platform. Applied Physics Letters, 104(2), 021116. doi:10.1063/1.4860983.
Boling Ouyang, Michael Haverdings, Roland Horsten, Marten Kruidhof, Pim Kat, and Jacob Caro, "Integrated photonics interferometric interrogator for a ring-resonator ultrasound sensor," Opt. Express 27, 23408-23421 (2019).
Shriram Sethuraman, James H. Amirian, Silvio H. Litovsky, Richard W. Smalling, and Stanislav Y. Emelianov, "Spectroscopic intravascular photoacoustic imaging to differentiate atherosclerotic plaques," Opt. Express 16, 3362-3367 (2008).
Krista Jansen, Antonius F. W. van der Steen, Heleen M. M. van Beusekom, J. Wolter Oosterhuis, and Gijs van Soest, "Intravascular photoacoustic imaging of human coronary atherosclerosis," Opt. Lett. 36, 597-599 (2011).
Kellnberger, S., Rosenthal, A., Myklatun, A., Westmeyer, G. G., Sergiadis, G., & Ntziachristos, V. (2016). Magnetoacoustic Sensing of Magnetic Nanoparticles. Physical Review Letters, 116(10), 108103. https://doi.org/10.1103/PhysRevLett.116.108103.
Wissmeyer, G., Pleitez, M.A., Rosenthal, A. et al. Looking at sound: optoacoustics with all-optical ultrasound detection. Light Sci Appl 7, 53 (2018). https://doi.org/10.1038/s41377-018-0036-7.
Cheng Zhang, Sung-Liang Chen, Tao Ling, & Guo, L. J. (2015). Review of Imprinted Polymer Microrings as Ultrasound Detectors: Design, Fabrication, and Characterization. IEEE Sensors Journal, 15(6), 3241-3248. doi:10.1109/jsen.2015.2421519.
C. Chao, L. J. Guo, S. Ashkenazi, and M. O'Donnell, "Ultrasound Detection Using Polymer Microring Resonators," in Conference on Lasers and Electro-Optics/Quantum Electronics and Laser Science and Photonic Applications Systems Technologies, Technical Digest (CD) (Optical Society of America, 2005), paper CTuH4.
Chen, Sung-Liang & Huang, S.C.-H & Ling, Tao & Ashkenazi, Shai & Guo, Lingjie. (2009). Polymer Microring Resonators for High-Sensitivity and Wideband Photoacoustic Imaging. IEEE transactions on ultrasonics, ferroelectrics, and frequency control. 56. 2482-91. 10.1109/TUFFC.2009.1335.
Govindan V, Ashkenazi S. Bragg waveguide ultrasound detectors. IEEE Trans Ultrason Ferroelectr Freq Control. Oct. 2012;59(10):2304-11. doi: 10.1109/TUFFC.2012.2455. PMID: 23143579.
Rosenthal, A., Kellnberger, S., Bozhko, D., Chekkoury, A., Omar, M., Razansky, D., & Ntziachristos, V. (2014). Sensitive interferometric detection of ultrasound for minimally invasive clinical imaging applications. Laser & Photonics Reviews, 8(3), 450-457. doi:10.1002/lpor.201300204.
Leinders, S., Westerveld, W., Pozo, J. et al. A sensitive optical micro-machined ultrasound sensor (OMUS) based on a silicon photonic ring resonator on an acoustical membrane. Sci Rep 5, 14328 (2015). https://doi.org/10.1038/srep14328.
Shai Tsesses, Daniel Aronovich, Assaf Grinberg, Evgeny Hahamovich, and Amir Rosenthal, "Modeling the sensitivity dependence of silicon-photonics-based ultrasound detectors," Opt. Lett. 42, 5262-5265 (2017).
Md. Faruque Hossain, Hau Ping Chan, and Mohammad Afsar Uddin, "Simultaneous measurement of thermo-optic and stress-optic coefficients of polymer thin films using prism coupler technique," Appl. Opt. 49, 403-408 (2010).
C. Chao, S. Ashkenazi, S. Huang, M. O'Donnell and L. Guo, "High-Frequency Ultrasound Sensors Using polymer microring resonators," IEEE Transactions on Ultrasonics, Ferroelectrics, and Frequency Control, vol. 54, No. 5, pp. 957-965, 2007.
Zhang, E., Laufer, J., & Beard, P. (2008). Backward-mode multiwavelength photoacoustic scanner using a planar Fabry-Perot polymer film ultrasound sensor for high-resolution three-dimensional imaging of biological tissues. Applied Optics, 47(4), 561. doi:10.1364/ao.47.000561.
De Brabander, G. N., Boyd, J. T., & Beheim, G. (1994). Integrated optical ring resonator with micromechanical diaphragms for pressure sensing. IEEE Photonics technology letters, 6(5), 671-673.
D. J. Lockwood and L. Pavesi, "Silicon photonics II: components and integration," Springer, 2011.
D.X. Xu, J. H. Schmid, G. T. Reed, G. Z. Mashanovich, D. J. Thomson, M. Nedeljkovic, X. Chen, D. Van Thourhout, S. Keyvaninia, and S. K. Selvaraja, "Silicon Photonic Integration Platform—Have We Found the Sweet Spot?", IEEE J. Sel. Top. Quantum Electron., vol. 20, No. 4, 8100217, 2014.
J. M. Cannata, T. A. Ritter, Wo-Hsing Chen, R. H. Silverman and K. K. Shung, "Design of efficient, broadband single-element (20-80 MHz) ultrasonic transducers for medical imaging applications," in IEEE Transactions on Ultrasonics, Ferroelectrics, and Frequency Control, vol. 50, No. 11, pp. 1548-1557, Nov. 2003, doi: 10.1109/TUFFC.2003.1251138.
Kopp, C., Bernabé, S., Bakir, B.B., Fédéli, J., Orobtchouk, R., Schrank, F., Porte, H., Zimmermann, L., & Tekin, T. (2011). Silicon Photonic Circuits: On-CMOS Integration, Fiber Optical Coupling, and Packaging. IEEE Journal of Selected Topics in Quantum Electronics, 17, 498-509.
J. L. Rose, "Ultrasonic guided waves in solid media," Cambridge University Press, 2014.
Md. Faruque Hossain, Hau Ping Chan, Abbas Z. Kouzani, and Md. Osman Goni, "Generalized characteristics of photo-elastic birefringence in polymer strip waveguides," Opt. Mater. Express 5, 1030-1044 (2015) https://doi.org/10.1364/OME.5.001030.
PCT International Search Report for International Application No. PCT/IL2019/050935, dated Dec. 15, 2019, 4pp.
PCT Written Opinion for International Application No. PCT/IL2019/050935, dated Dec. 15, 2019, 4pp.

* cited by examiner

POLYMER-COATED HIGH-INDEX WAVEGUIDE FOR ACOUSTIC SENSING

CROSS-REFERENCES TO RELATED APPLICATIONS

This application is a National Phase of PCT Patent Application No. PCT/IL2019/050935 having International filing date of Aug. 20, 2019, which claims the benefit of priority from U.S. Provisional Patent Application No. 62/720,050 to Rozental et al., entitled, "Polymer-coated high-index waveguide for ultrasound detection." The contents of the above applications are all incorporated by reference as if fully set forth herein in their entirety.

FIELD OF THE INVENTION

The present invention relates to the field of acoustic sensing and more specifically to ultrasound detection.

BACKGROUND

Ultrasound-based technologies are abundant in everyday life. These technologies enable non-destructive measurements of products and supply medical information through sonography. The detection of ultrasound is conventionally performed by piezoelectric transducers—electro-mechanical devices that generate a voltage in response to pressure transients. While piezoelectric transducers have been the enabling technology in medical ultrasonography, they exhibit inherent limitations that hinder the development of new applications. Piezoelectric transducers are both opaque and vulnerable to electromagnetic interference. In addition, the sensitivity of piezoelectric transducers scales with size, decreasing resolution and making them incompatible with several medical applications. For example, the performance of piezoelectric technology is often inadequate in applications such as intravascular photoacoustic imaging where both miniaturization and high sensitivity are desired, and/or in magnetoacoustics, where immunity to electromagnetic interference (EMI) is needed.

Interferometric ultrasound detection is an alternative to piezoelectric technology, where the intensity of the interference between two optical signals, one of which emanating from the detector, is modulated by an impinging ultrasound acoustic wave. Interferometric detectors are largely immune to electromagnetic interference and may be produced on transparent substrates. However, optical interferometry has yet to reach sub-Pascal sensitivities, in particular for applications such as optoacoustic imaging which is commonly achieved by large-area piezoelectric detectors (which also impose a resolution limit on these techniques).

SUMMARY

In accordance with some applications of the present invention, apparatus comprising an acoustic sensor having an optical sensing element, is provided. For some applications, the acoustic sensor comprises an ultrasound detector.

The acoustic sensor as provided by some applications of the present invention is particularly suitable for minimally invasive medical applications by allowing both miniaturization of the acoustic sensor while maintaining a high sensitivity of the sensor. In this context, in the specification and the claims "sensitivity" means the efficiency of conversion of an acoustic signal to an optical signal by the acoustic sensor. Additionally, the acoustic sensor as provided by some applications of the present invention, is generally immune to electromagnetic interference (EMI) further rendering it suitable for use in medical applications.

For some applications, the acoustic sensing element of the acoustic sensor comprises an optical waveguide. The optical waveguide typically comprises (a) a waveguide core (e.g., one or more waveguide cores) having a waveguide core refractive index and a waveguide core photo-elastic coefficient, and (b) an over-cladding comprising an optically transparent polymer coupled to the waveguide core and having an over-cladding refractive index and an over-cladding photo-elastic coefficient. Typically, the waveguide core refractive index is greater than the over-cladding refractive index, and the over-cladding photo-elastic coefficient is greater than the waveguide core photo-elastic coefficient.

For some applications, the waveguide core comprises an optical material characterized by a high refractive index, e.g., a refractive index of at least 1.7. Typically, the high waveguide core refractive index facilitates miniaturization of the acoustic sensor rendering the acoustic sensor suitable for use in various minimally invasive medical applications, e.g., intravascular ultrasound imaging. However, in accordance with some applications of the present invention, the waveguide core is additionally characterized by a relatively low photo-elastic coefficient. For example, the waveguide core comprises silicon which has a high refractive index of 3.48, and low photo-elastic coefficients of $-17.13$ $TPa^{-1}$ and $5.51$ $TPa^{-1}$ which may limit sensitivity of the optical waveguide. A low photo-elastic coefficient typically limits sensitivity of the waveguide because less refractive-index modulation occurs in the waveguide in response to an acoustic wave impinging on the waveguide, leading to reduced detection of the waveguide.

In accordance with some applications of the present invention, the waveguide core is immersed in an opto-mechanical material forming the over-cladding of the optical waveguide. The opto-mechanical material comprises a polymer, which is transparent to the light guided in the optical waveguide and has a photo-elastic coefficient greater than the photo-elastic coefficient of the material of which the waveguide core is made. Typically, the transparent polymer of the over-cladding has a high photo-elastic coefficient that is at least four times greater than the waveguide core photo-elastic coefficient. Additionally, the transparent polymer is characterized by a refractive index that is lower than the refractive index of the waveguide core. Further additionally, the transparent polymer is characterized by a Young Modulus of under 10 GPa, e.g., under 5 GPa.

For some applications, the transparent polymer of the over-cladding comprises Benzocyclobutene (BCB). The BCB is typically characterized by a relatively low refractive index of 1.54, and high photo-elastic coefficients of 99 $TPa^{-1}$ and 31 $TPa^{-1}$. Additionally, BCB has a Young Modulus of 2.9 GPa.

In accordance with some applications of the present invention, the transparent polymer over-cladding increases sensitivity of the optical waveguide by improving the conversion of the acoustic signal impinging upon the acoustic sensor into an optical signal thereby improving the detection of the acoustic waves by the apparatus. Consequently, both miniaturization (facilitated by the high refractive-index waveguide core), and enhanced sensitivity of the of the acoustic sensor (facilitated by the transparent polymer over-cladding), are achieved. Additionally, or alternatively, it is shown by the inventors elsewhere herein that the use of a transparent polymer over-cladding reduced susceptibility of the acoustic sensor to surface acoustic waves (SAWs) and acoustic reverberations. More specifically, it is shown by the inventors that a BCB over-cladding improves the capabilities of silicon-photonics waveguide for ultrasound detection in terms of sensitivity and susceptibility to acoustic reverberations and SAWs.

For some applications, a light source, e.g., a laser, is coupled to the optical waveguide and a reference optical signal from the laser interferes with the signal emanating from the waveguide. As an acoustic wave (e.g., an ultrasound wave) is incident upon the optical waveguide, it modifies a geometry and optical properties of the waveguide, such that the signal at its output acquires a modulation in its phase resulting in a different intensity of the interference with the reference optical signal. This modulation is indicative of the acoustic wave impinging upon the waveguide such that the acoustic waveform can be detected.

For some applications the optical waveguide further comprises and/or is coupled to (e.g., CROW), one or more resonators configured to exhibit an optical resonance at one or more wavelengths. For light propagating in the waveguide at the resonance wavelength, localization is obtained to the parts of the waveguide in which the resonator was fabricated and/or coupled to. Accordingly, the use of the resonators facilitates miniaturization of the acoustic sensor and enhances sensitivity.

For some applications, corrugation of the waveguide core may be used to expose a guided mode (transverse modes of a waveguide TE (transverse electrical) and TM (transverse magnetic)) to the opto-mechanical material (i.e., the transparent polymer).

There is therefore provided in accordance with some applications of the present invention, apparatus including: an acoustic sensor including an optical waveguide, the optical waveguide including: a waveguide core having a waveguide core refractive index and a waveguide core photo-elastic coefficient; an over-cladding layer coupled to the waveguide core and including an optically transparent polymer having an over-cladding refractive index and an over-cladding photo-elastic coefficient; the waveguide core refractive index is greater than the over-cladding refractive index, and the over-cladding photo-elastic coefficient is greater than the waveguide core photo-elastic coefficient.

For some applications, the over-cladding layer includes a bisbenzocyclobutene (BCB) over-cladding layer.

For some applications, the waveguide core refractive index is at least 1.7.

For some applications, a maximum magnitude of the photo-elastic coefficient of the waveguide core is 20 $TPa^{-1}$.

For some applications, the over-cladding refractive index is lower than 1.7.

For some applications, the over-cladding photo-elastic coefficient is at least 80 $TPa^{-1}$.

For some applications, the over-cladding photo-elastic coefficient is at least four times greater than the waveguide core photo-elastic coefficient.

For some applications, the optically transparent polymer of the over-cladding has a Young Modulus of under 10 (E) GPa.

For some applications, the optically transparent polymer of the over-cladding has a Young Modulus of under 5 (E) GPa.

For some applications, the waveguide core includes silicon.

For some applications, the apparatus further includes a light source arranged such that an optical signal generated by the light source and directed at the optical waveguide is modulated due to an acoustic wave impinging upon the optical waveguide.

For some applications, the light source includes a laser configured to generate a laser beam.

For some applications, the signal generated by the light source is modulate in phase.

For some applications, the signal generated by the light source is modulate in amplitude.

For some applications, the optical waveguide includes one or more optical resonators.

For some applications, the optical waveguide is the resonator.

For some applications, the one or more optical resonators are selected from the group consisting of: π phase-shifted Bragg grating (π-BG), Fabry-Perot cavity, and optical-ring resonator.

For some applications, a maximum length of the optical waveguide is 100 microns.

For some applications, the optical waveguide further includes an under-cladding layer.

There is additionally provided in accordance with some applications of the present invention, a system including: an optical waveguide including: a waveguide core having a waveguide core refractive index and a waveguide core photo-elastic coefficient; an over-cladding layer coupled to the waveguide core and including an optically transparent polymer having an over-cladding refractive index lower than the waveguide core refractive index, and an over-cladding photo-elastic coefficient greater than the waveguide core photo-elastic coefficient; an interferometer configured to generate, from a laser source, a laser beam directed at the optical waveguide such that the laser beam propagates through the optical waveguide, thereby modulating the laser beam by an acoustic wave impinging upon the optical waveguide.

For some applications, the interferometer is further configured to measure the modulation when the optical waveguide is being impinged by the acoustic wave, to calculate shifts in a spectral response of the optical waveguide based on the measuring, the shifts being indicative of a waveform of the acoustic wave.

For some applications, the optical waveguide includes one or more optical resonators.

For some applications, the optical waveguide core is the resonator.

For some applications, the one or more optical resonators are selected from the group consisting of: π phase-shifted Bragg grating (π-BG), Fabry-Perot cavity, and optical-ring resonator.

For some applications, the acoustic wave is an ultrasound acoustic wave.

For some applications, the over-cladding layer includes a bisbenzocyclobutene (BCB) over-cladding layer.

For some applications, the waveguide core refractive index is at least 1.7.

For some applications, a maximum magnitude of the photo-elastic coefficient of the waveguide core is 20 $TPa^{-1}$.

For some applications, the over-cladding refractive index is lower than 1.7.

For some applications, the over-cladding photo-elastic coefficient is at least 80 $TPa^{-1}$.

For some applications, the over-cladding photo-elastic coefficient is at least four times greater than the waveguide core photo-elastic coefficient.

For some applications, the optically transparent polymer of the over-cladding has a Young Modulus of under 10 (E) GPa.

For some applications, the optically transparent polymer of the over-cladding has a Young Modulus of under 5 (E) GPa.

For some applications, the waveguide core includes silicon.

There is further provided in accordance with some applications of the present invention, a method including: using an optical waveguide including: a waveguide core having a waveguide core refractive index and a waveguide core photo-elastic coefficient, and an over-cladding layer coupled to the waveguide core and including an optically transparent polymer having an over-cladding refractive index lower than the waveguide core refractive index, and an over-cladding photo-elastic coefficient greater than the waveguide core photo-elastic coefficient; directing a laser beam at the optical waveguide when the optical waveguide is impinged by an acoustic wave, to cause the laser beam to propagate through the optical waveguide such that the laser beam is modulated; and calculating shifts in a spectral response of the optical waveguide based on measuring the modulation, the shifts are indicative of a waveform of the acoustic wave.

For some applications, using the optical waveguide includes using the optical waveguide having a waveguide core refractive index of at least 1.7 and an over-cladding photo-elastic coefficient of at least 80 $TPa^{-1}$.

For some applications, the method further includes providing one or more optical resonators in the optical waveguide, the optical resonators selected from the group consisting of: $\pi$ phase-shifted Bragg grating ($\pi$-BG), Fabry-Perot cavity, and optical-ring resonator.

For some applications, the acoustic wave is an ultrasound acoustic wave.

For some applications, using the optical waveguide includes using the optical waveguide and the over-cladding includes a bisbenzocyclobutene (BCB) over-cladding layer.

For some applications, using the optical waveguide includes using the optical waveguide and the waveguide core includes silicon.

There is further provided in accordance with some applications of the present invention, apparatus including: an acoustic sensor including an optical waveguide, the optical waveguide including: a silicon waveguide core; an over-cladding layer coupled to the waveguide core and including an optically transparent polymer.

For some applications, the over-cladding layer includes a bisbenzocyclobutene (BCB) over-cladding layer.

For some applications, a photo-elastic coefficient of the optically transparent polymer is at least four times greater than a photo-elastic coefficient of the silicon waveguide core.

The present invention will be more fully understood from the following detailed description of embodiments thereof, taken together with the drawings, in which:

BRIEF DESCRIPTION OF THE DRAWINGS

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION OF APPLICATIONS

Figure 1:
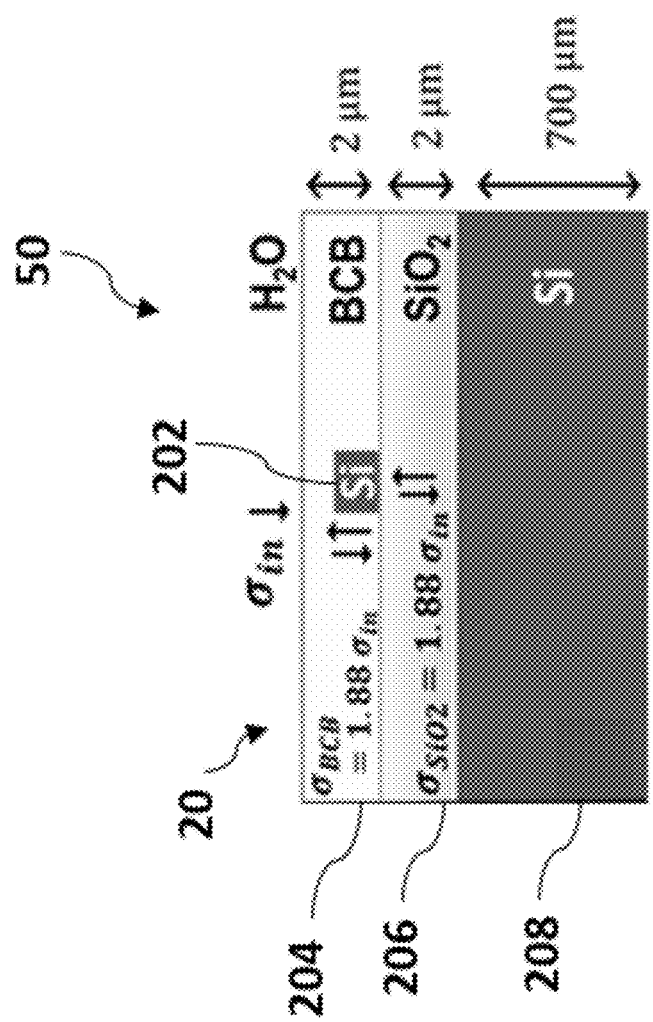
FIG. 1 is a schematic illustration showing a cross section of an apparatus comprising a waveguide having a silicon waveguide core that is embedded in an over-cladding comprising a transparent polymer, in accordance with some applications of the present invention.

Some aspects of the present invention provide an acoustic sensor configured for detection of acoustic waves by detecting the stress and strain it induces in an optical sensing element. The optical detection is typically based on a photo-elastic effect, where stress or strain in optical components of the acoustic sensor lead to changes in a refractive index of the optical components. These changes are indicative of the acoustic waves impinging upon the acoustic sensor, thereby allowing optical-based detection of the acoustic waves.

In some aspects of the present invention, the acoustic sensor comprises an ultrasound detector, e.g., an interferometric ultrasound detector. For some aspects, the ultrasound detector is configured for detection of ultrasound waves in a frequency of above 100 KHZ. The ultrasound detector is typically shaped, sized and oriented for ultrasound detection with medical applications. For example, intravascular photoacoustic imaging where both miniaturization and high sensitivity are desired, and/or in magnetoacoustics, where immunity to electromagnetic interference (EMI) is needed.

Some aspects of the present invention are directed to high-resolution ultrasound imaging, e.g. as part of a scanning device or an array of such detectors. This can be used to increase the resolution of medical imaging and non-destructive ultrasound testing. In particular, imaging catheters and endoscope can use the acoustic sensor provided herein in accordance with some aspects of the present invention, to increase the number of detectors employed and a frequency thereof, thus enabling imaging at a higher resolution. Some aspects of the present invention are especially suitable for hybrid ultrasound imaging techniques (e.g., optoacoustic and magnetoacoustic imaging), where it could increase resolution and consequently increase widespread use.

In some aspects of the present invention, the acoustic sensor comprises an optical waveguide comprising a waveguide core and a waveguide cladding coupled to, and embedding, the waveguide core.

In some aspects, the waveguide core has a waveguide core refractive index and a waveguide core photo-elastic coefficient. Typically, the waveguide core refractive index is a high refractive index of at least 1.7, and the waveguide core photo-elastic coefficient is a low photo-elastic coefficient of maximum 20 $TPa^{-1}$. For some applications, the waveguide core comprises a silicon waveguide core characterized by a high refractive index of 3.48. The high refractive index of silicon generally allows for miniaturization of the waveguide and consequently of the acoustic sensor. In contrast to the high refractive index of the silicon waveguide core, the silicon waveguide core is further characterized by low photo-elastic coefficients of $-17.13$ $TPa^{-1}$ and $5.51$ $TPa^{-1}$. The low photo-elastic coefficients may impair conversion of the acoustic signal impinging upon the acoustic sensor into an optical signal, thereby limiting sensitivity of the acoustic sensor.

In accordance with some aspects of the present invention, the above-mentioned drawbacks of the waveguide core are overcome by embedding the waveguide core in an over-cladding comprising a transparent polymer. Typically, the transparent polymer of the over-cladding is characterized by a relatively low refractive index of a maximum of 1.7, and a high photo-elastic coefficient of at least 30 $TPa^{-1}$. Typically, the high photo-elastic coefficient of the over-cladding allows for a high degree of deformation of the over-cladding by the acoustic wave impinging on the acoustic sensor, thereby increasing sensitivity of the acoustic sensor and compensating for the low sensitivity of the waveguide core. In some aspects, the over-cladding comprises a Benzocyclobutene (BCB), which is characterized by a refractive index of 1.54 and photo-elastic coefficients of 99 TPa-1 and 31 TPa-$^1$. In accordance with some aspects of the present invention, the inventors show herein that a Benzocyclobutene (BCB) over-cladding improve the capabilities of silicon-photonics waveguide for ultrasound detection in terms of sensitivity and susceptibility to acoustic reverberations and SAWs.

For some aspects of the present invention, a light source, e.g., a laser, is directed at the optical waveguide and a reference optical signal from the laser interferes with the signal emanating from the waveguide. As an acoustic wave (e.g., an ultrasound wave) is incident upon the optical waveguide, it modifies a geometry and optical properties of the waveguide, such that the signal at its output acquires a modulation in its phase, resulting in a different intensity of the interference with the reference optical signal. This modulation is indicative of the acoustic wave impinging upon the waveguide such that the acoustic waveform can be detected.

In accordance with some aspects of the present invention the apparatus further comprises an interferometer for use with the optical waveguide. The interferometer is configured to generate, from the laser source, a laser beam directed at the optical waveguide such that the laser beam propagates through the optical waveguide, thereby modulating the laser beam by the acoustic wave impinging upon the optical waveguide. This modulation is indicative of the acoustic wave impinging upon the waveguide such that the acoustic waveform can be detected.

In accordance with some aspects of the present invention, the optical waveguide further comprises and/or is coupled to (e.g., CROW), one or more optical resonators configured to exhibit and optical resonance at one or more wavelength. For light propagating in the waveguide at the resonance wavelength, localization is obtained to the parts of the waveguide in which the resonator was fabricated or coupled to. Accordingly, the use of the resonators typically facilitates miniaturization of the acoustic sensor and enhances sensitivity. For some applications, the one or more optical resonators are selected from the group consisting of: π phase-shifted Bragg grating (π-BG), Fabry-Perot cavity, and optical-ring resonator.

In accordance with some aspects of the present invention, a method for detection of acoustic waves is provided comprising directing a laser beam at the optical waveguide when the optical waveguide is impinged by an acoustic wave, to cause the laser beam to propagate through the optical waveguide such that the laser beam is modulated. Accordance to some aspects of the present invention, the waveguide comprises a high refractive index waveguide core (e.g., a silicon core) embedded in a transparent polymer over-cladding. Shifts in a spectral response of the optical waveguide based on measuring the modulation are calculated. These shifts are typically indicative of a waveform of the acoustic wave, thereby enabling detecting the acoustic waves.

Reference is now made to FIG. 1, which is a schematic illustration modeling a cross section of an optical acoustic sensor 50 comprising a waveguide 20. Waveguide 20 is shown having a silicon waveguide core 202 that is embedded in an over-cladding 204 comprising a transparent polymer, in accordance with some applications of the present invention.

For some applications, waveguide 20 comprises a waveguide core 202 comprising silicon and an over-cladding 204 comprising Benzocyclobutene (BCB). It is noted that the silicon waveguide core and/or the BCB over-cladding are shown by way of illustration and not limitation. Waveguide core 202 may comprise any other optical material characterized by a relatively high refractive index and a relatively low photo-elastic coefficient. Similarly, over-cladding 204 may comprise any other suitable transparent polymer. Optionally but not necessarily, waveguide 20 additionally comprises a silica under-cladding 206 which is typically a substrate on which the waveguide core is fabricated. Optionally but not necessarily, waveguide 20 comprises an additional silicon substrate 208.

Waveguide core 202 of waveguide 20 is typically characterized by a high refractive index and a low photo-elastic coefficient, and over-cladding 204 is typically characterized by a low refractive index, a high photo-elastic coefficient, and a Young Modulus of under 10 (E) GPa, e.g., under 5 GPa.

In particular, the refractive index of waveguide core 202 is greater than the refractive index of over-cladding 204, and the photo-elastic coefficient of over-cladding 204 is greater (e.g., 4 times greater) than the photo-elastic coefficient of waveguide core 202. The following Table 1 shows optical, mechanical, acoustical, and photo-elastic properties of Silicon (Si), Silica (SiO2), and Benzocyclobutene (BCB):

| Property | Si | SiO$_2$ | BCB |
|---|---|---|---|
| Refractive index (n) | 3.48 | 1.44 | 1.54 |
| Young Modulus (E) GPa | 130 | 76.7 | 2.9 |
| Poisson Ratio (v) | 0.27 | 0.19 | 0.34 |
| Density (ρ) Kg/m$^3$ | 2328 | 2200 | 1050 |
| Acoustic impedance (W) Kgm$^{-2}$s$^{-1}$ | 19.5 × 10$^6$ | 13.6 × 10$^6$ | 2.17 × 10$^6$ |
| Photo-elastic constant (C1) TPa$^{-1}$ | −17.13 | 1.17 | 99 |
| Photo-elastic constant (C2) TPa$^{-1}$ | 5.51 | 3.73 | 31 |

For the purpose of experiments conducted in accordance with some applications of the present invention, waveguide 20 was fabricated having a silicon core and a BCB over-cladding. In some cases, waveguide 20 was compared to other waveguides also having a silicon core but lacking the BCB over-cladding. The term "silicon waveguide" used herein generally refers to a waveguide comprising a silicon core.

Fabrication of the Silicon Waveguides (e.g., as Illustrated in FIG. 1):

Fabrication of the silicon waveguides was performed at the foundry of IMEC (Leuven, Belgium) using the SOI multi-project wafer services of ePIXfab. The fabrication was performed on 200 mm SOI wafers with deep ultraviolet at the wavelength of 193 nm and inductively coupled plasma reactive ion etching. Two types of wafers were provided, in which the same silicon structures were produced. In both wafers, the silicon substrate had a thickness of 700 μm. In the first wafer, the silicon core was buried in a silica cladding In accordance with some application of the present invention, in the second wafer, used to produce the structure shown in FIG. 1, the core was covered by a protective resist, which was replaced by BCB (3022-35 series, The Dow Chemical Company) using the following procedure. The resist cladding was removed using acetone and the exposed wafer was spin-coated with BCB at 3000 rpm for 60 seconds, resulting in a BCB layer with a thickness of approximately 2 μm. This was followed by baking on a hotplate at 120 degrees C. for 10 minutes to remove solvents and to stabilize the BCB film. Afterwards, the film underwent a curing process at 230 degrees C. for 30 minutes in inert atmosphere while flowing N2 gas was used to prevent oxidation.

In both wafers, 2 mm long silicon waveguides were produced with fiber-to-chip grating couplers on both ends. Polarization maintaining (PM) fibers were coupled to the waveguides where the orientation of the fiber with respect to the grating coupler determined whether the TE or TM mode would be launched. In total, 4 fiber-coupled chips were produced for the discussed options of polarization (TE or TM) and over-cladding material (silica, or, as in accordance with applications of the present invention, a BCB over-cladding).

It is to be appreciated that with regard to fabrication of the silicon waveguides described hereinabove, numerical values are provided by way of illustration and not limitation. Typically, but not necessarily, each value shown is an example selected from a range of values that is within 20% of the value shown. Similarly, although certain steps are described with a high level of specificity, a person of ordinary skill in the art will appreciate that other steps may be performed, mutatis mutandis.

Reference is still made to FIG. 1. In accordance with some applications of the present invention, waveguide 20 (comprising strip silicon waveguide core 202 embedded in a BCB over-cladding 204), was examined and compared to a waveguide comprising a silica over-cladding, without an over-cladding comprising a transparent polymer, e.g., BCB, and thus having a silicon core and an over-cladding having low photo-elastic coefficients of 1.17 and 3.73 TPa$^{-1}$. For experiments performed in accordance with applications of the present invention, both the waveguides (i.e., waveguide 20 and a waveguide without an over-cladding of a transparent polymer), were immersed in water and the values for the width and height of the silicon core were chosen to be 500 nm and 220 nm, respectively, whereas the total thickness of the cladding was 4 μm.

As noted above, in accordance with some applications of the present invention, experiments were conducted using waveguide guide 20 as modeled in FIG. 1 and using the silicon core waveguide with a silica over-cladding. In general, experiments were conducted by the inventors at least in order to compare the sensitivity and susceptibility to SAWs and acoustic reverberations in both types of waveguides. The experiments were conducted considering longitudinal acoustic waves that impinge on the two types of waveguides perpendicularly, i.e. the acoustic propagation is in the y direction. Denoting the acoustic impedance by W, the transmission of the normal stress, σy, from medium "1" to medium "2" is given by:

$$t = \frac{2W2}{W1 + W2}, \tag{1}$$

whereas the reflection is given by $$r = \frac{W2 - W1}{W1 + W2}. \tag{2}$$

To calculate the strain in the device layer, which is the sum of the waves propagating in the y and −y directions, one needs to account for the multiple reflections between the different interfaces, e.g., for all the multiple reflections between the different interfaces. The analysis, provided in in equations A1-A4 below, shows that in the waveguide with the absence of the BCB over-cladding, the normal stress in the SiO2 over-cladding layer is equal to $1.86\sigma_{in}$, where $\sigma_{in}$ is the y component of the stress of the incident wave. In accordance with some application of the present invention, for waveguide 20 (FIG. 1), the normal stress in both the SiO2 (under-cladding) and BCB (over-cladding) layers was calculated to be $1.88\sigma_{in}$, i.e. almost identical to the value obtained for the waveguide with only the silica over-cladding and without the BCB over-cladding.

Expressions for $\sigma_y$ in the SiO$_2$ and BCB layers of the silicon waveguides were calculated. In the analysis, it was assumed that the widths of the silica and BCB layers are considerably smaller than the acoustic wavelength, enabling calculating the effect of multiple reflections without accounting for the phase accumulated by the acoustic waves. For simplicity, notations "$t_{a \to b}$" and "$r_{a \to b}$" were used to respectively denote the transmission and reflection from layer a to layer b, where the expressions for the transmission and reflection coefficients are given in Eqs. 1 and 2. For waveguide 20, the normal stress in the SiO$_2$ layer is given by $$\sigma_{SiO2} = \frac{t_{H2O \to SiO2}(1 + r_{SiO2 \to Si})}{1 - r_{SiO2 \to Si} r_{SiO2 \to H2O}} \sigma_{in}, \tag{A1}$$

Substituting the expressions in Eqs. 1 and 2 in Eq. A1, the following was obtained:

$$\sigma_{SiO2} = \frac{2W_{Si}}{(W_{Si} + W_{H2O})}\sigma_{in}. \quad (A2)$$

Interestingly, the expression in Eq. A2 represents the transmission from water to silicon that would have been obtained if no SiO2 layer were present. In waveguide 20, the normal stress in the SiO2 and BCB layers is given by the following expression:

$$\sigma_{BCB/SiO2} = \frac{t_{H2O \to BCB}t_{BCB \to SiO2}r_{SiO2 \to Si}t_{SiO2 \to BCB}(1 + r_{BCB \to H2O})}{1 - r_{BCB \to H2O}r_{BCB \to SiO2}}\sigma_{in}. \quad (A3)$$

Substituting the again expressions in Eqs. 1 and 2, Eq. A3 may be written explicitly by $$\sigma_{BCB/SiO2} = \frac{(W_{SiO2} + W_{Si})(W_{H2O} + W_{BCB})(W_{SiO2}^2 - W_{BC}^2) - 8W_{H2O}W_{SiO2}W_{BCB}(W_{Si} - W_{SiO2})}{(W_{H2O} + W_{SiO2})(W_{SiO2} + W_{Si})(W_{H2O} + W_{BCB})(W_{SiO2} + W_{BCB})}\sigma_{in}. \quad (A4)$$

It is noted that the normal stress is identical in both the BCB and $SiO_2$ layers since the derivation of Eqs. 1 and 2 was based on a continuous transition of the normal stress between layers.

Two connected metrics are frequently used to quantify the effect of mechanical perturbations on the optical properties of a waveguide. When the change is detected in optical phase ($\phi$) in a waveguide of a given length due to uniform pressure (P), the phase sensitivity: $S\phi=d\phi/dP$, is used. For applications in which a resonator is used, the normalized sensitivity is more appropriate: $S\lambda=d\lambda res/(\lambda res\ dP)$, where $\lambda res$ is the resonance wavelength and $d\lambda res$ is the shift in wavelength due to the perturbation. $S\lambda$ may be calculated by using the following equation:

$$S_\lambda = \frac{1}{n_{eff}}\frac{dn_{eff}}{dP} + \frac{d\varepsilon_z}{dP} \quad (3)$$

where neff is the refractive index of guided mode and $\varepsilon z$ is the strain in the z direction. The relation between $S\lambda$ and $S\phi$ is given by $$S_\phi = \frac{2\pi n_{eff}L}{\lambda}S_\lambda \quad (4)$$

where $\lambda$ is the incident light wavelength and L is the effective length of the sensor.

To calculate $S\lambda$ due to a plane longitudinal acoustic wave that impinges on the chip perpendicularly, we use the below model in which $\varepsilon z$, $\varepsilon x \to 0$. The calculation of $S\lambda$ is performed by computing the change in neff of the guided mode due to deformation and change in the refractive index of the materials by the photo-elastic effect, given by the following equations:

$$\sigma_x = \frac{v}{1-v}\sigma_y \quad (5.a)$$

$$\varepsilon_y = -\frac{(1+v)(1-2v)}{(1-v)}\sigma_y \quad (5.b)$$

$$\Delta n_x = \frac{(C_1 v + V_2)}{1-v}\sigma_y \quad (5.c)$$

$$\Delta n_y = \frac{[(1-v)C_1 + 2vC_2]}{1-v}\sigma_y \quad (5.d)$$

where $C_1$ and $C_2$ are the photo-elastic constants and v is the Poisson ratio. The values of the optical, mechanical, and acoustic parameters of silicon, silica, and BCB are summarized above in Table 1. It is noted that for Si and SiO2, the optical parameters were measured at $\lambda=1550$ nm, whereas for BCB their values were obtained at $\lambda=1536$ nm. The calculation of $S\lambda$ via Eqs. (3) and (5) used a mode solver to find the perturbations to the effective refractive index. In accordance with some applications of the present invention, COMSOL Multiphysics was used and the analysis was conducted for waveguide 20 and for waveguide with the silica over-cladding and without the BCB over-cladding, for both the TE the TM modes. For the wavelength $\lambda=1540$ nm, the values obtained for the TM and TE modes were $n_{eff}=1.78$ and $n_{eff}=2.46$, respectively, for the silica over-cladding and $n_{eff}=1.84$ and $n_{eff}=2.47$, respectively, for the BCB over-cladding (waveguide 20, FIG. 1).

Figures 2A, 2B:
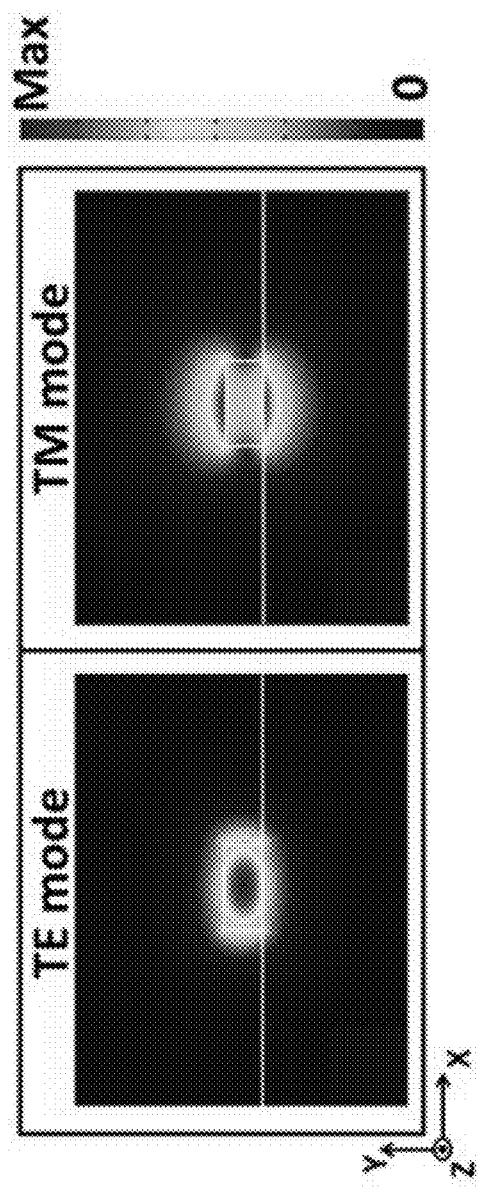
FIGS. 2A-B show the magnitude of the electric field, |E|, for the TE (FIG. 2A) and TM (FIG. 2B) modes of the silicon waveguide of FIG. 1, in accordance with some applications of the present invention.

Reference is now made to FIGS. 2A-B which show the magnitude of the electric field, |E|, for the TE (FIG. 2A) and TM (FIG. 2B) modes of waveguide 20, in accordance with some applications of the present invention.

Figure 3:
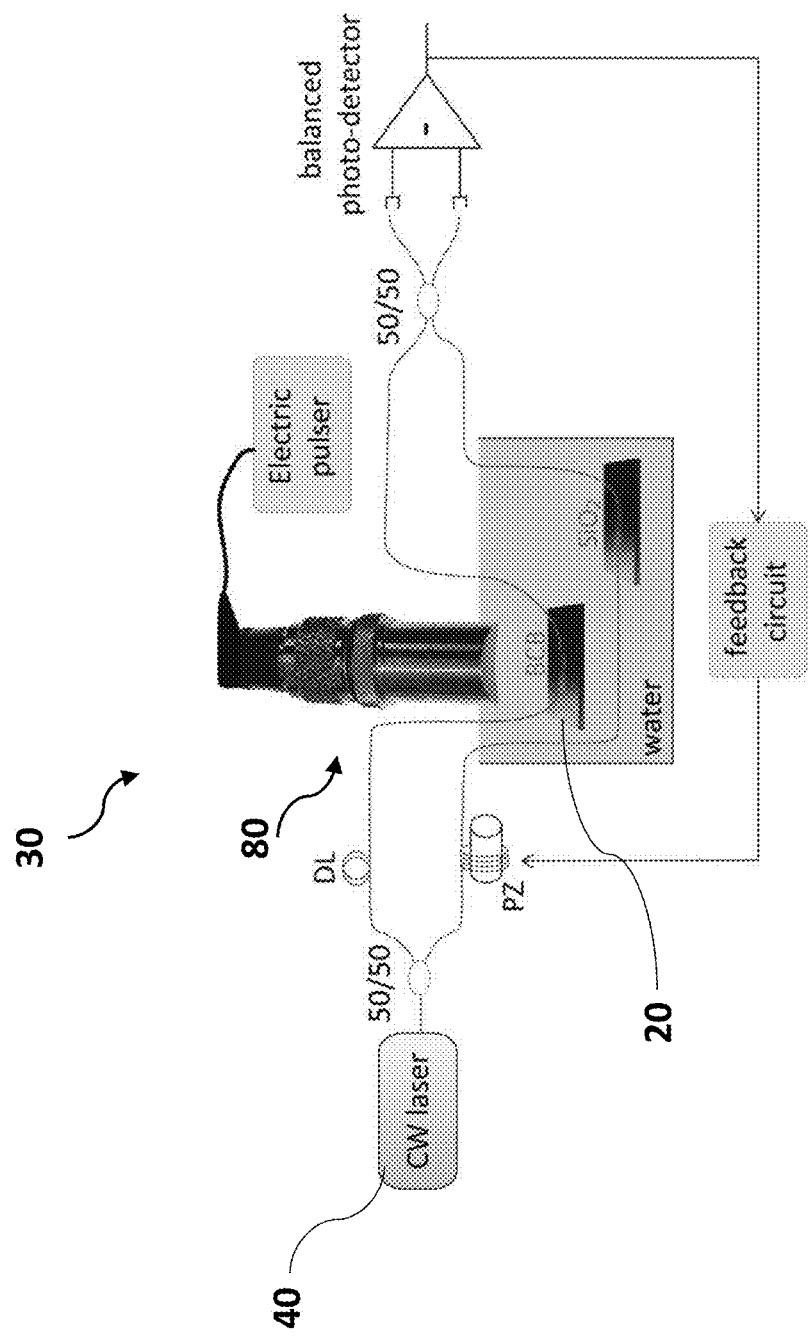
FIG. 3 is a schematic illustration of an interferometer utilizing the waveguide of FIG. 1, in accordance with some applications of the present invention.

Reference is now made to FIG. 3 which is a schematic illustration of an interferometer ultrasound detection system comprising an interferometer 30 utilizing waveguide 20 of FIG. 1, in accordance with some applications of the present invention. Waveguide 20 is compared to a waveguide having a silicon core and a silica over-cladding (without the transparent polymer over-cladding), In the experimental setup, shown in FIG. 3, for each of the polarizations, the examined silicon waveguides each having a different over-cladding materials (i.e., waveguide 20 and the waveguide with the silica over-cladding and without a BCB over-cladding) were connected to two arms of a Mach-Zehnder interferometer 30 and immersed in a water bath. For each of the polarizations, a Mach-Zehnder interferometer was constructed, where in each of the interferometer arms a silicon-core waveguide with a different over-cladding material (BCB as in FIG. 1, or silica) was connected. An ultrasound transducer 80 was used to generate acoustic waves that impinged on only one of the silicon-core waveguides, which were separated by more than 10 cm. The interferometer included a continuous-wavelength laser 40 (AP3350A, Apex Technologies), which was tuned to $\lambda=1540$ nm, a balanced photo-detector (PDB450C, Thorlabs), and a fiber stretcher, where all the components in interferometer used polarization-maintaining fibers. The interferometer was locked to quadrature point using a feedback circuit connected to the fiber stretcher and photo-detector. The acoustic waves were generated by a cylindrically focused ultrasound transducer 80 with a diameter of 12.7 mm, focal length of 25.76 mm, and a central frequency of 15 MHz (V319, Olympus), which was connected to an electric pulser. In each measurement, the acoustic waves impinged on only one of the waveguides, and the resulting phase variations was determined from the readout of the balanced photo-detector. To characterize the acoustic beam, a calibrated needle hydrophone with a diameter of 40 μm, bandwidth of 30 MHz, and calibration accuracy of ±15% (Precision Acoustics) was scanned along the focus of the transducer to characterize the generated acoustic beam, yielding a maximum peak-to-peak pressure of approximately 1.3 MPa in the focus, a focal full-width-at-half-maximum (FWHM) of 0.4 mm.

Figures 4A, 4B:
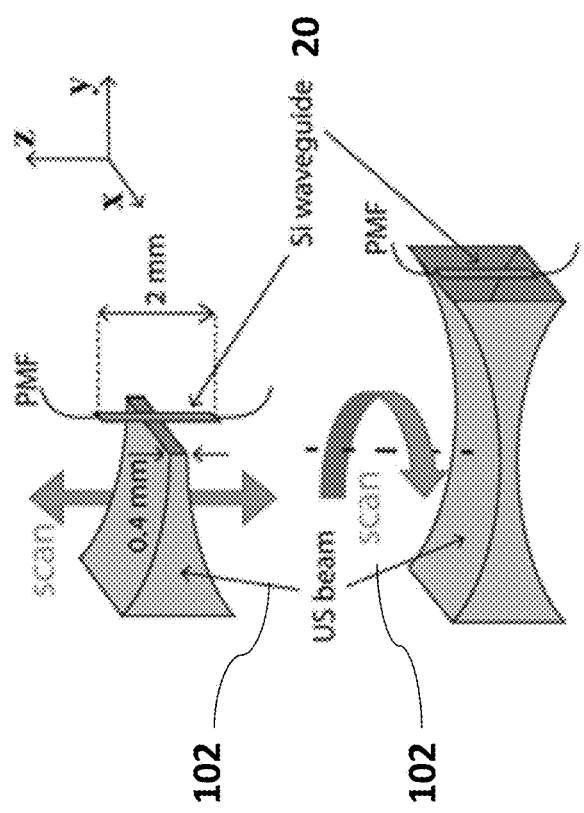
FIGS. 4A-B are schematic illustrations showing a schematic diagram of an experimental setup, using the apparatus and conducted in accordance with some applications of the present invention.

Reference is now made to FIGS. 4A-B which show a schematic diagram of an additional experimental setup, conducted in accordance with some applications of the present invention. In the experimental setup shown in FIGS. 4A-B, an ultrasound (US) beam 102 focused in one dimension was generated using a cylindrically focused US transducer (shown in FIG. 3) whereas the detection was performed with the silicon waveguide with either type of over cladding (i.e., for waveguide 20 with the BCB over-cladding, compared to the waveguide with the silica over-cladding without a BCB over-cladding) for both the TE and TM modes, where polarization-maintaining fibers (PMFs) were used to couple it to an interferometric system that measured the US-induced phase modulation in the waveguide. The substrate of the strip waveguide is not shown in FIGS. 4A-B. In the experimental set up of FIG. 4A, in order to measure sensitivity S$\lambda$, the waveguide was positioned at the focus of the transducer, at a distance of 25.76 mm, where scanning in the x and z directions was used to position the beam in the center of the waveguide. In the experimental set up of FIG. 4B, in order to assess the effect of surface acoustic waves (SAWs) on the waveguide, the waveguide was positioned in the far field of the transducer at a distance of 49 mm, where the wavefront of the US beam was approximately planar over the length of the waveguide. Since the excitation of SAWs require an incidence angle of approximately 20 degrees, the US beam was rotated around the z axis.

The phase modulation of the light guided in the four silicon-core waveguides was measured in two acoustic configurations. In the first configuration, the acoustic wave was focused in the z direction on the center of the waveguide, as illustrated in FIG. 4A. The waveguide was scanned in the x and z directions, and the phase modulation due to the ultrasound burst was recorded for the position in which the acoustic beam was symmetrically centered on the waveguide. To compare the response of the silicon waveguide to that of the fibers, the acoustic beam was subsequently scanned away from the silicon waveguide, approximately 5 mm in the z direction, such that its focus lied entirely on the optical fibers. In the second configuration (FIG. 4B), the goal was to excite the SAW in the chips by an approximately planar acoustic wave that hits the chips at an angle of approximately 20°. Accordingly, the chip was moved to the far-field of the acoustic beam at a distance of approximately 49 mm from the transducer. The transducer was rotated around the z axis, creating an angle of θ with the normal to the chip (y axis in FIG. 4B), where the scanning in θ was performed from 0 to 30°. For each angle, the transducer was scanned in the x direction to find the position of strongest signal.

Figure 5B:
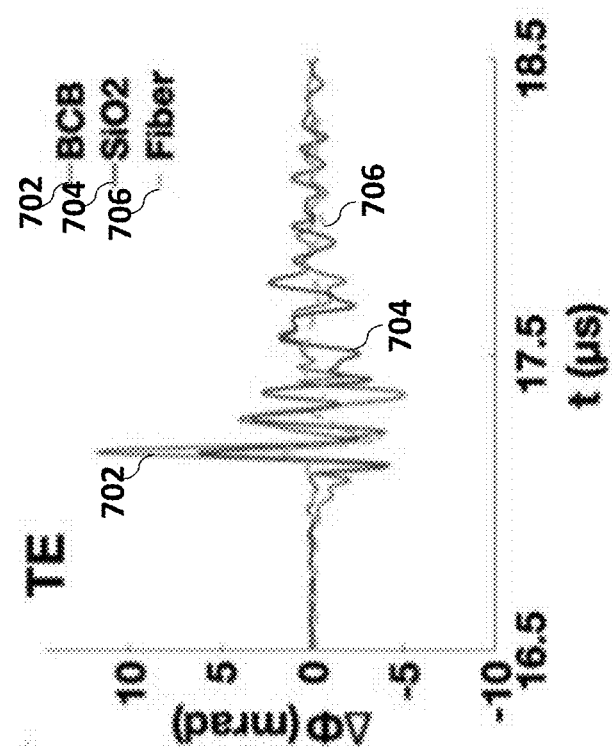
FIGS. 5A-B are graphs showing measured optical phase shifts in silicon waveguides as compared to optical phase shifts obtained from fibers, resulting from a focused ultrasound burst impinging upon the waveguide and the fibers, respectively. The results are shown for the waveguide with the BCB over-cladding (as shown in FIG. 1), in accordance with some applications of the present invention, and as compared to a silica ($SiO_2$) over-cladding, and to the fibers for both the TM (FIG. 5A) and TE (FIG. 5B) modes.
Figure 5A:
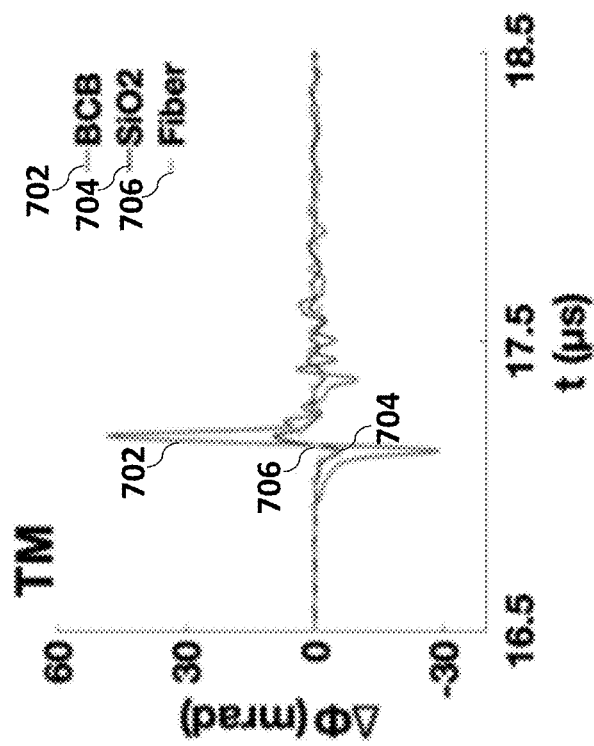

Reference is now made to FIGS. 5A-B which are graphs showing measured optical phase shifts in the silicon waveguides due to a focused ultrasound burst impinging upon the waveguides, and the optical phase shifts obtained from fibers. The results are shown for waveguide 20, with the BCB over-cladding, in accordance with some applications of the present invention, as compared to SiO$_2$ over-cladding, and from the fibers, for both the TM (FIG. 5A) and TE (FIG. 5B) modes. In graphs 5A-B, line 702 represents the results for the BCB over-cladding, line 704 represents the results for the SiO$_2$ over-cladding, and line 706 represents the results for the fibers.

FIGS. 5A-B show the phase difference between the two interferometer arms, ΔΦ, in response to longitudinal acoustic waves measured using the geometry of FIG. 4A for TM (FIG. 5A) and TE (FIG. 5B) waveguides with the BCB (waveguide 20) and silica over-cladding. The responses for the waveguides are compared to the signals obtained when the ultrasound beam was focused on the fibers (dashed curve). The results in FIGS. 5A-B show that for the TE mode, compared to SiO2 over-cladding, the BCB over-cladding enhanced the signal by a factor of 1.41, whereas for the TM mode, an enhancement of 4.98 was achieved. While in both polarization, the SiO2- and BCB-coated (i.e., over-cladding) waveguides produced signals with the same polarity, since these two waveguides were on opposing arms of the same interferometer (FIG. 3), the result of FIGS. 5A-B show not only enhancement in magnitude, but also reversed polarity for the individual phase perturbations of each waveguide. Using Eq. (4) and the effective refractive indices of the different configurations, the measured enhancement in S_$\lambda$ due to the BCB over-cladding for the TE and TM modes were −1.4 and −4.82, respectively, where the minus sign relates to the reversed polarity of the signals. Using our theoretical model, and accounting for a 10 nm fabrication error in each of the dimensions of the waveguide, the theoretical values obtained for the enhancement in S$\lambda$ were −1.13±0.27 and −3.9±2.3 for the TE and TM modes, respectively, in good agreement with the magnitude of the experimental values. As FIGS. 5A-B show, and in accordance with some applications of the present invention, the signal enhancement of the BCB-coated silicon waveguide with respect to the optical fibers was even higher; in terms of S$\lambda$ the magnitude of the enhancement was 1.44 and 9.41 for the TE and TM modes, assuming an neff=1.47 for the optical fiber in Eq. (4).

To determine the origin of the differences in the responses of the different waveguides, the numerical simulations were repeated for S_$\lambda$ with [ε]_y=0 instead of Eq. 5.b, i.e. without accounting for the contribution of the core deformation to the overall sensitivity. R was defined as the ratio between S_$\lambda$ of the reduced model with [ε]_y=0 to that of the full model of Eqs. 5.a-5.d. For TM polarization, R=2.4×10^(−2) and R=1.27 for the SiO2- and BCB-coated waveguides, were obtained. FIGS. 5A-B show that in the SiO2-coated TM waveguide, the response was almost exclusively due to the deformation of the core. In contrast, and in accordance with some applications of the present invention, in the BCB-coated TM waveguide, the response was mostly due to the photo-elastic effect of the transparent polymer over cladding (in this case BCB) The result of R>1 for the BCB-coated waveguide shows that S_$\lambda$ would have been higher if no deformation of the core occurred ([ε]_y=0), or alternatively that the effect of deformation acts in the opposite direction to the photo-elastic effect and reduces the overall response. For TE polarization, R=−0.57 and R=3.6 for the SiO2- and BCB-coated waveguides, were obtained. Again, in the BCB-coated waveguide (waveguide 20), R>1 was obtained typically due to the photo-elastic effect and waveguide deformation being in opposite directions. In the SiO2-coated waveguides, R<0 was obtained since the response for [ε]_y=0 had an opposite sign to that of the total response, indicating that the contribution of the waveguide deformation was larger in magnitude than of that of the photo-elastic effect and had an opposite sign.

Figure 6B:
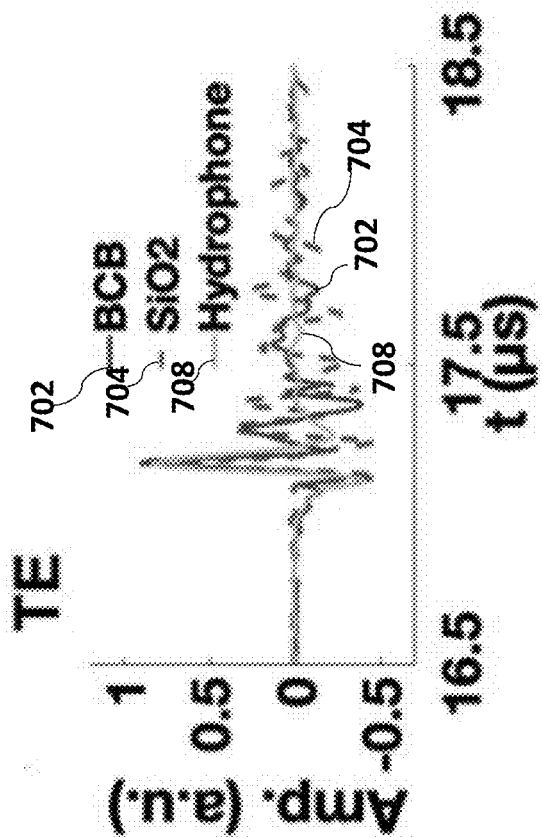
FIGS. 6A-B are graphs showing a normalized response from silicon waveguides compared to the hydrophone response due to a focused ultrasound burst. The results given are the hydrophone response in comparison with the waveguides with the BCB over-cladding (as shown in FIG. 1), in accordance with some applications of the present invention, and as compared to a $SiO_2$ over-cladding for both the TM (FIG. 6A) and TE (FIG. 6B) modes.
Figure 6A:
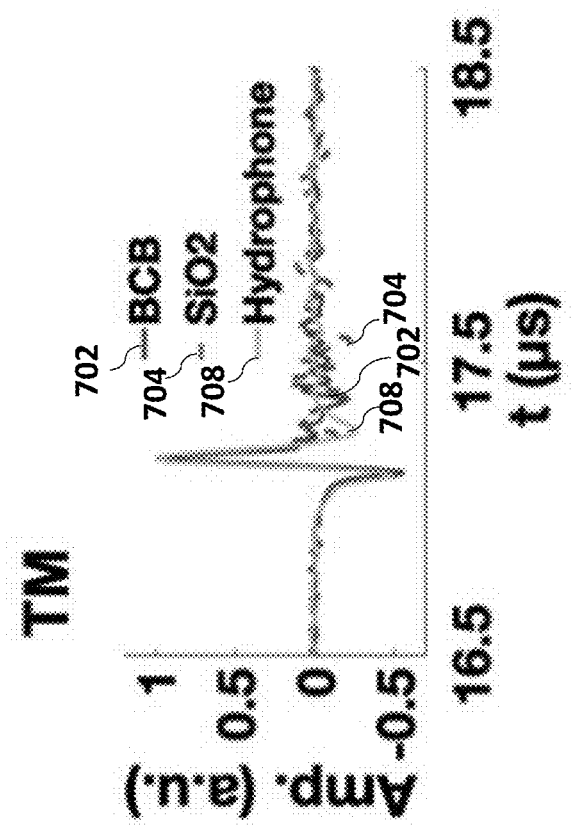

Reference is now made to FIGS. 6A-B which are graphs showing a normalized response from silicon waveguides compared to the hydrophone response due to a focused ultrasound burst. The results given are the hydrophone response in comparison with the silicon waveguides with the BCB over-cladding (waveguide 20 of FIG. 1, in accordance with some applications of the present invention) and $SiO_2$ over-cladding, for both the TM (FIG. 6A) and TE (FIG. 6B) modes, in accordance with some applications of the present invention. In graphs 6A-B, line 702 represents the results for the BCB over-cladding, line 704 represents the results for the $SiO_2$ over-cladding, and line 708 represents the results for the hydrophone response.

In FIGS. 6A-B, the responses of the waveguides were normalized and compared them to the response obtained from the hydrophone measurement. Since the dimensions of the hydrophone were different than those of the silicon waveguides, the hydrophone response was averaged over a scan length of 2 mm in the z direction centered on the transducer focus, effectively emulating the spatial-averaging effect experienced by the 2 mm long waveguide. As shown in FIGS. 6A-B, the initial bipolar signal was almost identical for all the waveguides and exhibited the same profile as the signal measured by the hydrophone. For both the TM and TE modes, the accompanying reverberations were reduced when the BCB over-cladding was used. Examining the peak-to-peak value of the reverberations after t=17.5 µs in FIGS. 6A-B, the following values were obtained: 0.16 (TM-BCB), 0.34 (TM-SiO2), 0.16 (TE-BCB), 0.5 (TE-SiO2).

Since the initial bipolar signal measured with the silicon waveguides represent the average acoustic signal integrated over a length of 2 mm, the sensitivity $S\lambda$ of the BCB-coated waveguide 20 may be quantified using the hydrophone measurement. While the peak-to-peak pressure at the focus of the transducer was 1.3 MPa, the average signal over the 2 mm length was 0.26 MPa, leading to $S\_\phi=0.31$ rad $MPa^{-1}$ and $S\_\phi=0.055$ rad $MPa^{-1}$ for the BCB-coated TM and TE waveguides, respectively. Using Eq. 4 and accounting for the hydrophone calibration accuracy, one obtains $S\_\lambda=(21\pm3.2)\times10^{-6}$ $MPa^{-1}$ and $S\_\lambda=(2.7\pm0.41)\times10^{-6}$ $MPa^{-1}$ for the BCB-coated TM and TE waveguides, respectively.

Figure 7A:
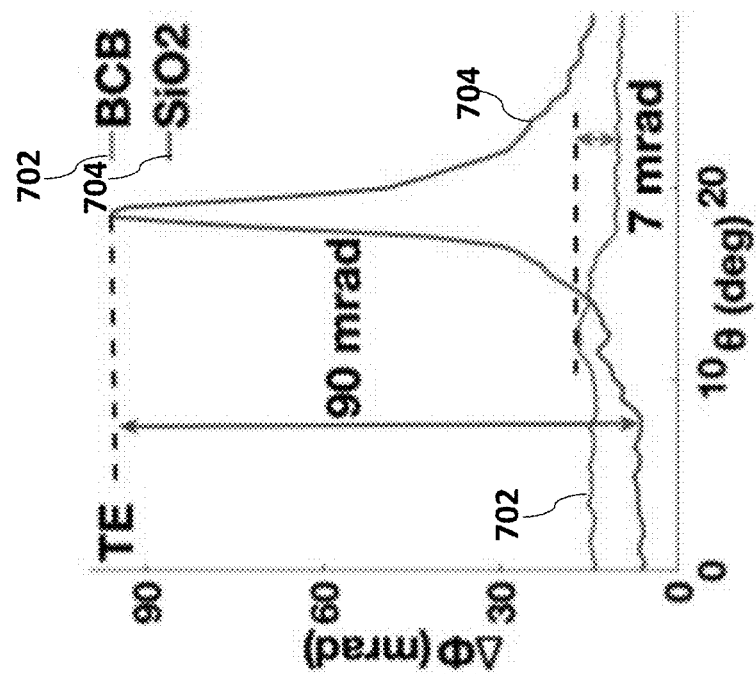
FIGS. 7A-B are graphs showing measured peak-to-peak values of the ultrasound-induced phase shifts in the far-field measurement illustrated in FIG. 4B obtained for the waveguides with BCB over-cladding, in accordance with some applications of the present invention, and as compared to $SiO_2$ over-cladding for TM (FIG. 7A) and TE (FIG. 7B) modes.
Figure 7B:
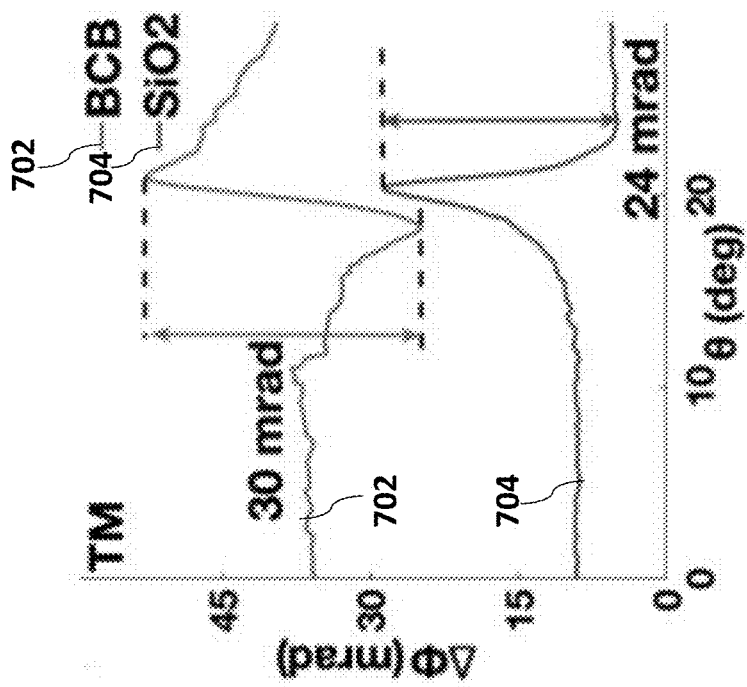

Reference is now made to FIGS. 7A-B which are graphs showing measured peak-to-peak values of the ultrasound-induced phase shifts in the far-field measurement illustrated in FIG. 4B obtained for the waveguides with BCB over-cladding (waveguide 20 as shown in FIG. 1), in accordance with some applications of the present invention) and $SiO_2$ over-cladding (without a BCB over-cladding), for TM (FIG. 7A) and TE (FIG. 7B) modes. In graphs 7A-B, line 702 represents the results for the BCB over-cladding and line 704 represents the results for the $SiO_2$ over-cladding.

FIGS. 7A-B show the peak-to-peak phase values obtained as a function of angle in the second acoustic configuration in which the response to SAWs was assessed (FIG. 4B). The results are shown for BCB or silica-coated (i.e., over-cladded) waveguide cores for the TM (FIG. 7A) and TE (FIG. 7B). The effect of SAWs is visible in FIGS. 7A-B as the large variations in the signal around the angle of 20 degrees. As shown, SAWs dominate the response of the silica-cladding chips for the TE mode, whereas the response for the TM mode is more moderate. For the waveguides with the BCB over-cladding, the response of the TM mode to SAWs was comparable in magnitude to that of the silica-cladding chips, whereas in the TE waveguide the effect of SAWs was diminished by over an order of magnitude. It is noted that that while the responses in FIGS. 7A-B, which were measured in the far field, also include the contribution of phase perturbation in the fibers in the proximity of the silicon core waveguides, the clear qualitative and quantitative differences between the responses may be solely attributed to susceptibility of the silicon waveguides to SAWs.

Figure 8:
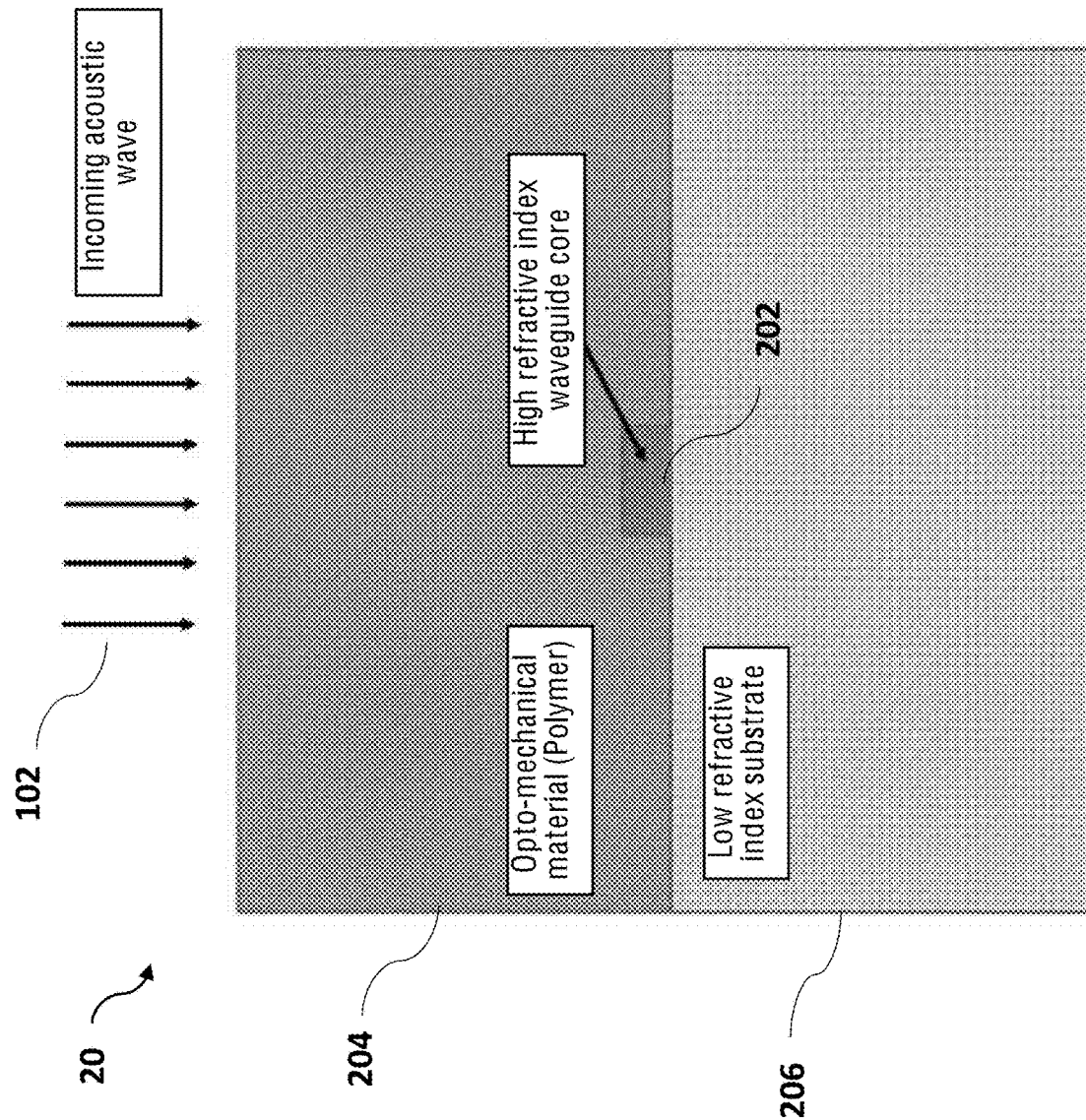
FIG. 8 is a schematic showing a cross section of a waveguide core embedded in an over-cladding comprising a transparent polymer, in accordance with some applications of the present invention.

Reference is now made to FIG. 8, which is a schematic illustration of waveguide 20, in which waveguide core 202 is shown to be placed on low refractive index substrate 206 and embedded in over-cladding 204, in accordance with some applications of the present invention. FIG. 8 shows waveguide 20 lacking the additional silicon substrate layer 208 shown in FIG. 1. It is noted that other types of implementations of waveguide 20 are possible, in accordance with some applications of the present invention (e.g., a ridge waveguide and/or a hollow waveguide).

Reference is again made to FIGS. 1A-8. As shown, in FIGS. 1A-8, it is experimentally demonstrated by the inventors that an over cladding comprising a transparent polymer characterized by a high photo-elastic coefficient, e.g., a BCB over-cladding, can significantly improve the capabilities of silicon-photonics waveguide for ultrasound detection in terms of sensitivity and susceptibility to acoustic reverberations and SAWs.

For longitudinal waves, the enhancement in $S\lambda$ was approximately 4.82 for the TM mode and 1.4 for the TE mode. As shown, the effect of reflection and refraction in the cladding due to acoustic impedance mismatches, were taken into account. As shown, the effect of BCB on the propagation of the acoustic waves is negligible and the enhancement in $S\lambda$ may be solely attributed to the changes in the optical properties of the waveguides for a given value of $\sigma\_y$ (Eqs. 5.a-5.d) rather than to mechanical enhancement in $\sigma\_y$ due to acoustic propagation effects. As shown, both for polarizations, the sensitivity of the BCB-coated waveguides was mostly due to the photo-elastic effect, where the effect of the waveguide deformation was with an opposite sign and thus reduced the overall response. While in the TM waveguide, this reduction in sensitivity, calculated via $100\%\times(1-R^{-1}))$, was relatively small and was equal to merely 21% (R=1.27), in the TE waveguide the reduction was much more significant and reached 72% (R=3.6), leading to a much weaker total response. The higher weight of the photo-elastic effect in the response of the BCB-coated TM waveguide may be explained by the spatial distribution of its mode (FIG. 2B), whose overlap with the BCB over-cladding is more significant than in the case of the TE mode. It is noted that in the case of the SiO2-coated waveguides, the total response was mostly due to deformations in the waveguide core structure, leading to a total response with an opposite polarity to the one obtained for the BCB-coated waveguides.

Although results shown herein relate to an acoustic wave with normal incidence, the angular dependence of the acoustic response was additionally experimentally studied by the inventors to evaluate the effect of SAWs. For SAWs, the use of a BCB over-cladding led to an order of magnitude reduction in the response of the TE mode, whereas for the TM mode the magnitude of the response did not change considerably. Nonetheless, because of its significant enhancement in sensitivity to longitudinal waves, the relative susceptibility of the TM mode to SAWs was also significantly reduced by the BCB coating.

In all the measurements, the initial bipolar signal detected by the silicon waveguides was accompanied by acoustic reverberations, which may be explained by the impedance mismatch between the silicon substrate and its surrounding.

Since the speed of sound in silicon is approximately 8400 m/s, the acoustic roundtrip in the 700 μm thick silicon substrate was 0.17 μs, comparable to the duration of the ultrasound burst, as measured by the hydrophone. Thus, the leading edge of the pulse directly detected by the waveguide experiences a delay of 0.17 μs before its echo from the back of the silicon substrate is detected again, overlapping with the trailing edge of the original pulse. Because of this overlap, the reverberations appear continuously in the measured signals, rather than at isolated time instances. In both the TE and TM waveguides, the use of BCB for the over-cladding reduced the effect of reverberations, where the weakest effect was obtained for the BCB-coated TM waveguides. Further reduction in the effect of the reverberation may be achieved by using an additional lossy backing layer with high acoustic impedance, similar to those used in piezoelectric transducers, or by locally thinning of the silicon substrate below the waveguides to a thickness that is considerably smaller than the acoustic wavelength.

In terms of sensitivity, the $S\_\lambda$ achieved shown herein for the BCB-coated TM waveguide is approximately 50% higher than a value tested for a polystyrene micro-ring, $13.5 \times [10]^{(-6)}$ $MPa^{(-1)}$ (results not shown). It is note that that $S\_\lambda$ is a property of the waveguide and does not depend on the propagation length, enabling a valid comparison between waveguides used in different configurations.

In accordance with some applications of the present invention, further enhancement in $S\lambda$, beyond the one shown herein may be achieved by exposing more of the guided mode to the polymer over-cladding or using over-cladding materials with higher photo-elastic coefficients than those of BCB. While in principle one may use the water surrounding the chip as the over-cladding material by exposing the silicon core, this approach has several limitations. First, water and silicon are incompatible materials in terms of optical transparency. While silicon-photonics devices usually operate at telecom wavelengths owing to the opacity of silicon to visible light, the absorption coefficient of water exceeds 5 dB/cm for wavelengths above 1,200 nm and reaches 50 dB/cm at 1,550 nm, which hinders the production of high-Q resonators. Second, exposing the silicon core may limit clinical applications in which the sensor needs to be in contact with tissue or bodily fluids. Therefore, in some applications of the present invention, an over-cladding with materials characterized by a higher photo-elastic coefficients than that of BCB, is used.

Reference is still made to FIGS. 1A-8. In order to fully optimize sensitivity and applicability, both high-level fabrication capabilities are required as well as high photo-elastic coefficients of materials used in fabrication. Some applications of the present invention provide configurations that enable miniaturization without the need for structure fabrication in the polymer structure. In some applications, this is enabled by a combination of one or more material characteristics e.g., high Q-factor of materials, high refractive indices and high photo-elastic coefficients of polymers. Such a combination is far from trivial, depending heavily on a suitable choice of parameters that boost the effects of the cladding material on the overall mode for the specific type of ultrasound perturbation. In some applications, combinations based on the concepts described herein provide a gain of up to a factor of 5 over non-BCB over-cladding guides.

A potential advantage in an acoustic sensor described herein is in that the in terms of fabrication simplicity, repeatability and low-cost compatible with mass production. This potential advantage stems from the fabrication process of a sensor as described herein, which is compatible with CMOS fabrication technology, which is the backbone of the mass production capabilities of the electronics industry It is to be noted that for some applications, techniques and apparatus described in the following publications are combined with techniques and apparatus described herein:

Rosenthal et al. "Embedded ultrasound sensor in a silicon-on-insulator photonic platform" Appl. Phys. Lett. 104, 021116 (2014); and Ouyang et al. "Integrated photonics interferometric interrogator for a ring-resonator ultrasound sensor Vol. 27, Issue 16, pp. 23408-23421 (2019)

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
an acoustic sensor comprising an optical waveguide, the optical waveguide comprising:
a waveguide core having a waveguide core refractive index and a waveguide core photo-elastic coefficient;
an over-cladding layer coupled to the waveguide core and comprising an optically transparent polymer having an over-cladding refractive index and an over-cladding photo-elastic coefficient;
wherein the waveguide core refractive index is greater than the over-cladding refractive index, and a magnitude of the over-cladding photo-elastic coefficient is greater than a magnitude of the waveguide core photo-elastic coefficient.

2. The apparatus according to claim 1, wherein the over-cladding layer comprises a bisbenzocyclobutene (BCB) over-cladding layer.

3. The apparatus according to claim 1, wherein the waveguide core refractive index is at least 1.7.

4. The apparatus according to claim 1, wherein a maximum magnitude of the photo-elastic coefficient of the waveguide core is 20 $TPa^{-1}$.

5. The apparatus according to claim 1, wherein the over-cladding refractive index is lower than 1.7.

6. The apparatus according to claim 1, wherein the over-cladding photo-elastic coefficient is at least four times greater than the waveguide core photo-elastic coefficient.

7. The apparatus according to claim 1, wherein the optically transparent polymer of the over-cladding has a Young Modulus of under 10 (E) GPa.

8. The apparatus according to claim 1, wherein the waveguide core comprises silicon.

9. The apparatus according to claim 1, further comprising a light source arranged such that an optical signal generated by the light source and directed at the optical waveguide is modulated due to an acoustic wave impinging upon the optical waveguide.

10. The apparatus according to claim 9, wherein the light source comprises a laser configured to generate a laser beam.

11. The apparatus according to claim 9, wherein the signal generated by the light source is modulate in phase.

12. The apparatus according to claim 9, wherein the signal generated by the light source is modulate in amplitude.

13. The apparatus according to claim 1, wherein the optical waveguide comprises one or more optical resonators.

14. The apparatus according to claim 13, wherein the optical waveguide is the resonator.

15. The apparatus according to claim 13, wherein the one or more optical resonators are selected from the group consisting of: π phase-shifted Bragg grating (π-BG), Fabry-Perot cavity, and optical-ring resonator.

16. A system comprising:
an optical waveguide comprising:
a waveguide core having a waveguide core refractive index and a waveguide core photo-elastic coefficient;
an over-cladding layer coupled to the waveguide core and comprising an optically transparent polymer having an over-cladding refractive index lower than the waveguide core refractive index, and a magnitude of the over-cladding photo-elastic coefficient greater than a magnitude of the waveguide core photo-elastic coefficient;
an interferometer configured to generate, from a laser source, a laser beam directed at the optical waveguide such that the laser beam propagates through the optical waveguide, thereby modulating the laser beam by an acoustic wave impinging upon the optical waveguide.

17. The system according to claim 16, wherein the interferometer is further configured to measure the modulation when the optical waveguide is being impinged by the acoustic wave, to calculate shifts in a spectral response of the optical waveguide based on the measuring, the shifts being indicative of a waveform of the acoustic wave.

18. The system according to claim 16, wherein the optical waveguide comprises one or more optical resonators.

19. Apparatus comprising:
an acoustic sensor comprising an optical waveguide, the optical waveguide comprising:
a waveguide core having a waveguide core refractive index and a waveguide core photo-elastic coefficient;
an over-cladding layer coupled to the waveguide core and comprising an optically transparent polymer having an over-cladding refractive index and an over-cladding photo-elastic coefficient;
wherein the waveguide core refractive index is greater than the over-cladding refractive index, and the over-cladding young modulus is at least one order of magnitude smaller than the waveguide core young modulus.

20. The Apparatus of claim 19, wherein the optically transparent polymer of the over-cladding has a Young Modulus of under 10 (E) GPa.

* * * * *